(12) United States Patent
Roberts et al.

(10) Patent No.: US 11,040,041 B2
(45) Date of Patent: *Jun. 22, 2021

(54) METHOD OF TREATING PULMONARY ARTERIAL HYPERTENSION

(71) Applicant: Cipla (UK) Limited, Weybridge (GB)

(72) Inventors: Karl Roberts, Llanelli (GB); Geena Malhotra, Mumbai (IN); Dhiraj Abhyankar, Mumbai (IN); Kalpana Joshi, Maharashtra (IN); Jeevan Ghosalkar, Maharashtra (IN)

(73) Assignee: Cipla (UK) Limited, Weybridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/749,244

(22) Filed: Jan. 22, 2020

(65) Prior Publication Data

US 2020/0155557 A1 May 21, 2020

Related U.S. Application Data

(63) Continuation of application No. 15/230,803, filed on Aug. 8, 2016, now Pat. No. 10,576,083.

(30) Foreign Application Priority Data

Aug. 13, 2015 (IN) .......................... 3058/MUM/2015

(51) Int. Cl.
| | |
|---|---|
| *A61K 31/519* | (2006.01) |
| *A61K 31/497* | (2006.01) |
| *A61K 31/44* | (2006.01) |
| *A61K 31/34* | (2006.01) |
| *A61K 31/505* | (2006.01) |
| *C07D 401/04* | (2006.01) |
| *A61K 31/33* | (2006.01) |
| *A61K 31/35* | (2006.01) |
| *A61K 9/20* | (2006.01) |
| *A61K 9/00* | (2006.01) |
| *A61K 31/496* | (2006.01) |
| *A61K 31/352* | (2006.01) |
| *A61K 31/435* | (2006.01) |
| *A61K 31/551* | (2006.01) |

(52) U.S. Cl.
CPC .......... *A61K 31/519* (2013.01); *A61K 9/2054* (2013.01); *A61K 9/0019* (2013.01); *A61K 31/352* (2013.01); *A61K 31/435* (2013.01); *A61K 31/496* (2013.01); *A61K 31/551* (2013.01)

(58) Field of Classification Search
CPC ..................................................... A61K 31/519
USPC ..................................................... 514/264.1
See application file for complete search history.

(56) References Cited

U.S. PATENT DOCUMENTS

| | | | |
|---|---|---|---|
| 2012/0196881 A1* | 8/2012 | Najarian ............... | A61K 31/198 514/269 |
| 2013/0210733 A1 | 8/2013 | Morgans, Jr. et al. | |
| 2013/0251787 A1* | 9/2013 | Nicolls ................ | A61K 31/197 424/450 |
| 2014/0296244 A1* | 10/2014 | Gerber .................. | A61K 31/53 514/250 |

OTHER PUBLICATIONS

Baylor Scott and White Health, "What is Pulmonary Hypertension?", http://www.sw.org/medicine/pulmonary/ph-pah-differences, printed Jan. 17, 2018.
Corena-McLeod, Maria, "Comparative Pharmacology of Risperidone and Paliperidone" Drugs R D, vol. 15, No. 2, pp. 163-174, 2015.
Dempsie, et al., "Pulmonary hypertension: therapeutic targets within the serotonin system", British Journal of Pharmacology, vol. 155, pp. 455-462, 2008.
Dweik, Raed A. et al., "Pulmonary Hypertension", Cleveland Clinic Center for Continuing Education, Disease Management, 2011.
Zhang, et al., "Sarpogrelate hydrochloride, a serotonin 5HT2A receptor antagonist, ameliorates the development of chronic hypoxic pulmonary hypertension in rats", J. Anesth, 2015, pp. 715-723.

* cited by examiner

*Primary Examiner* — Shengjun Wang
(74) *Attorney, Agent, or Firm* — Meunier Carlin & Curfman LLC

(57) ABSTRACT

The present invention is concerned with the treatment of Pulmonary Arterial Hypertension (PAH) by administering Paliperidone. The instant invention further relates to use of a pharmaceutical composition comprising Paliperidone, for the treatment of PAH.

12 Claims, No Drawings

METHOD OF TREATING PULMONARY ARTERIAL HYPERTENSION

CROSS REFERENCE TO RELATED APPLICATIONS

This application is a continuation of U.S. application Ser. No. 15/230,803, filed Aug. 8, 2016, which claims benefit of Indian Application 3058/MUM/2015, filed Aug. 13, 2015, the contents of which are incorporated by reference.

FIELD OF THE INVENTION

The present invention relates to method of treating Pulmonary Arterial Hypertension. It specifically relates to the method of treating Pulmonary Arterial Hypertension using Paliperidone.

BACKGROUND

Pulmonary arterial hypertension (PAH) is a life-threatening and progressive disease of various origins characterized by pulmonary vascular remodeling that leads to increased pulmonary vascular resistance and pulmonary arterial pressure, most often resulting in right-sided heart failure. It is a progressive condition characterized by elevated pulmonary arterial pressures leading to right ventricular (RV) failure. The most common symptom is breathlessness, with impaired exercise capacity being the hallmark of the disease.

It is associated with significant morbidity and mortality, which is caused by complex pathways that culminate in structural and functional alterations of the pulmonary circulation and increases in pulmonary vascular resistance and pressure. The progressive narrowing of the pulmonary arterial bed results from an imbalance of vasoactive mediators, including prostacyclin, nitric oxide, and endothelin-1. This leads to an increased right ventricular afterload, right heart failure, and premature death. Diverse genetic, pathological, or environmental triggers, stimulate PAH pathogenesis, culminating in vasoconstriction, cell proliferation, vascular remodeling, and thrombosis.

Over the past two decades, significant advances in the understanding of the pathophysiology of PAH have led to the development of several therapeutic targets in this disease. Besides conservative therapeutic strategies such as anticoagulation and diuretics, the current treatment paradigm for PAH, targets the mediators of the three main biologic pathways that are critical for its pathogenesis and progression: endothelin receptor antagonists inhibit the upregulated endothelin pathway by blocking the biologic activity of endothelin-1; phosphodiesterase-5 inhibitors prevent breakdown and increase the endogenous availability of cyclic guanosine monophosphate, which signals the vasorelaxing effects of the downregulated mediator nitric oxide; and prostacyclin derivatives provide an exogenous supply of the deficient mediator prostacyclin.

There are various drugs approved for the treatment of PAH. Inotropic agents such as digoxin aids in the treatment by improving the heart's pumping ability. Nifedipine (Procardia) and Diltiazem (Cardizem) act as vasodilators and lowers pulmonary blood pressure and may improve the pumping ability of the right side of the heart.

Bosentan (Tracleer), ambrisentan (Letairis), macitentan (Opsumit), etc. are dual endothelin receptor antagonist that help to block the action of endothelin, a substance that causes narrowing of lung blood vessels. There are others which dilate the pulmonary arteries and prevent blood clot formation. Examples of such drugs are Epoprostenol (Veletri, Flolan), treprostinil sodium (Remodulin, Tyvaso), iloprost (Ventavis); PDE 5 inhibitors such as Sildenafil (Revatio), tadalafil (Adcirca), relaxes pulmonary smooth muscle cells, which leads to dilation of the pulmonary arteries.

In addition to these established current therapeutic options, a large number of potential therapeutic targets are being investigated. These novel therapeutic targets include soluble guanylyl cyclase, phosphodiesterases, tetrahydrobiopterin, 5-hydroxytryptamine (serotonin) receptor 2B, vasoactive intestinal peptide, receptor tyrosine kinases, adrenomedullin, rho kinase, elastases, endogenous steroids, endothelial progenitor cells, immune cells, bone morphogenetic protein and its receptors, potassium channels, metabolic pathways, and nuclear factor of activated T cells.

Considering the current treatment approaches mentioned in the prior art, there still remains a need to develop different and more effective treatment approaches in a cost effective and a time efficient manner. Giving due consideration to the diversity of the drugs that are in existence, a way forward could be to determine the activity of the existing drugs to address life threatening diseases such as PAH.

SUMMARY OF THE INVENTION

The present invention is concerned with the treatment of Pulmonary Arterial Hypertension (PAH) by administering Paliperidone. The instant invention further relates to use of a pharmaceutical composition comprising Paliperidone, for the treatment of PAH.

DETAILED DESCRIPTION OF THE INVENTION

Paliperidone (9-hydroxy-risperidone), is a psychotropic agent belonging to the chemical class of benzisoxazole derivatives. It is a monoaminergic antagonist that exhibits the characteristic dopamine $D_2$ and serotonin (5-hydroxytryptamine type 2A) antagonism. Esters of paliperidone at the 9-hydroxy position are also known. Paliperidone palmitate is the palmitate ester of paliperidone. Paliperidone palmitate is hydrolyzed to Paliperidone, which is the primary active metabolite of the older antipsychotic Risperidone. U.S. Pat. No. 6,320,048 is concerned with preparation of a number of such 3-piperidinyl-1,2-benzisoxazoles having antipsychotic activity and preparation thereof. Paliperidone palmitate is the chemically known as Hexadecanoic acid 3-[2-[4-(6-fluoro-1,2-benzisoxazol-3-yl)piperidin-1-yl]ethyl]-2-methyl-4-oxo-6,7,8,9-tetrahydro-4H-pyrido[1,2-a]pyrimidin-9-yl ester and has structure as given below.

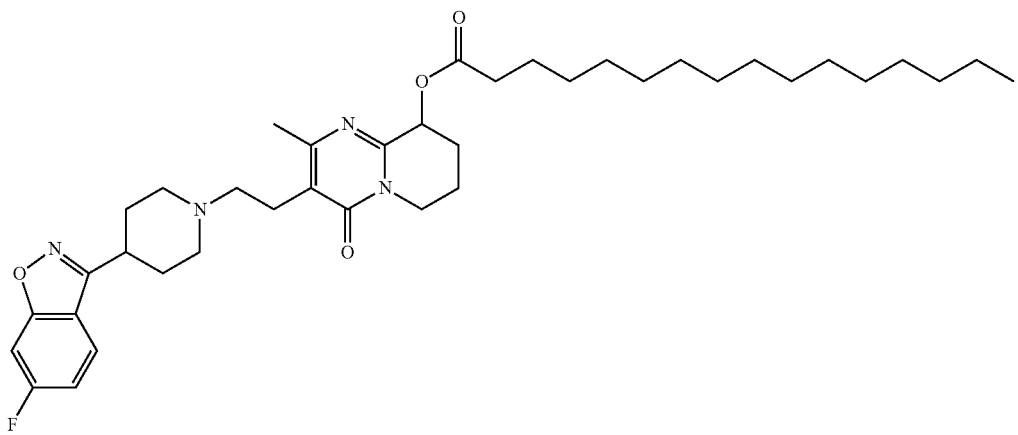 [SMILES: CCCCCCCCCCCCCCCC(=O)OC1CCCn2c1nc(C)c(CCN1CCC(c3noc4cc(F)ccc34)CC1)c2=O]

Paliperidone Palmitate

Paliperidone has been approved for the treatment of schizophrenia. It has also been approved for the treatment of schizoaffective disorder as monotherapy and as an adjunct to mood stabilizers or antidepressants. Extended release (ER) osmotic controlled release oral delivery (OROS) paliperidone, as a tablet formulation, is marketed in the United States (U.S.) by Janssen Pharms, as Invega®.

Paliperidone palmitate was formulated as an aqueous nano suspension as is described in U.S. Pat. Nos. 6,577,545 and 6,555,544. Invega Sustenna®, the innovator product of Paliperidone Palmitate marketed by Janssen Pharms is available as a white to off-white aqueous extended-release injectable suspension for intramuscular injection in dose strengths of 39 mg, 78 mg, 117 mg, 156 mg, and 234 mg paliperidone palmitate. A 3 month long acting depot formulation, Invega Trinza® (273 MG, 410 MG, 546 MG, and 819 MG paliperidone palmitate), has been recently approved by FDA. It is indicated for the treatment of the patients after they have been adequately treated with Invega Sustenna®, for at least 4 months.

Paliperidone is an antagonist of the dopamine $D_2$ receptor, serotonin 5-HT2A receptor, α1 and α2 adrenergic receptors, and H1 histaminergic receptor. Paliperidone has virtually no affinity for cholinergic muscarinic M1 or β1- and β2-adrenergic receptors.

Dopamine has been recognized as an important modulator of central as well as peripheral physiologic functions in both humans and animals. Dopamine receptors have been identified in a number of organs and tissues, which include several regions within the central nervous system, sympathetic ganglia and postganglionic nerve terminals, various vascular beds, the heart, the gastrointestinal tract, and the kidney. The peripheral dopamine receptors influence cardiovascular and renal function by decreasing afterload and vascular resistance and promoting sodium excretion. Within the kidney, dopamine receptors are present along the nephron, with highest density on proximal tubule epithelial cells. It has been reported that there is a defective dopamine receptor, especially D(1) receptor function, in the proximal tubule of various animal models of hypertension as well as in humans with essential hypertension. Recent reports have revealed the site of and the molecular mechanisms are responsible for the defect in D(1) receptors in hypertension. Moreover, recent studies have also demonstrated that the disruption of various dopamine receptor subtypes and their function produces hypertension in rodents (Exp Biol Med (Maywood). 2003 February; 228(2):134-42).

$5-HT_{2A}$ is expressed widely throughout the central nervous system (CNS). It is expressed near most of the serotoninergic terminal rich areas, including neocortex (mainly prefrontal, parietal, and somatosensory cortex) and the olfactory tubercle. Especially, high concentrations of this receptor on the apical dendrites of pyramidal cells in layer V of the cortex may modulate cognitive processes, working memory and attention. In the periphery, it is highly expressed in platelets and many cell types of the cardiovascular system, in fibroblasts, and in neurons of the peripheral nervous system. Additionally, $5-HT_{2A}$ mRNA expression has been observed in human monocytes.

Physiological processes mediated by the receptor include:
CNS: neuronal excitation, behavioral effects, learning and anxiety
Smooth muscle: contraction (in gastrointestinal tract & bronchi)
Vasoconstriction/vasodilation
Platelets: aggregation
Activation of the 5-HT2A receptor with DOI produces potent anti-inflammatory effects in several tissues including cardiovascular and gut. Other 5-HT2A agonists like LSD also have potent anti-inflammatory effects against TNF-alpha-induced inflammation.
Activation of the 5-HT2A receptor in hypothalamus causes increases in hormonal levels of oxytocin, prolactin, ACTH, corticosterone, and renin.
Role in memory The inventors of the instant invention have found that dopamine Type 2 ($D_2$) antagonist and serotonin Type 2 (5HT2A) activity of Paliperidone has a role to play in the treatment of pulmonary arterial hypertension (PAH).

Pulmonary arterial hypertension (PAH) refers to a clinical syndrome of vascular disease with a stereotyped pattern of histopathology and is related to a variety of secondary disease states. Pulmonary arterial hypertension (PAH) is a chronic condition, which affects the heart and lungs. The disease is also known as high blood pressure of the lungs.

It is a progressive disorder associated with significant morbidity and mortality, is caused by complex pathways that culminate in structural and functional alterations of the pulmonary circulation and increases in pulmonary vascular resistance and pressure.

Diverse genetic, pathological, or environmental triggers stimulate PH pathogenesis culminating in vasoconstriction, cell proliferation, vascular remodeling, and thrombosis. Current concepts suggest that PH pathogenesis involves three primary processes: vasoconstriction, cellular proliferation/vascular remodeling, and thrombosis. The molecular mechanism of pulmonary arterial hypertension (PAH) is not known yet, but it is believed that the endothelial dysfunction results in a decrease in the synthesis of endothelium-derived vasodilators such as nitric oxide and prostacyclin. Moreover, there's a stimulation of the synthesis of vasoconstrictors such as thromboxane and vascular endothelial growth factor (VEGF). These results in a severe vasoconstriction and smooth muscle and adventitial hypertrophy characteristic of patients with PAH.

Pulmonary hypertension can be classified as either primary or secondary. When the arterial hypertension is not accompanied or caused by another underlying heart or lung disease or condition, it is called primary pulmonary hypertension. When the arterial hypertension is triggered by another disease state, it is designated secondary pulmonary hypertension. Exemplary conditions which can cause secondary pulmonary hypertension include congenital heart defects, ventricular or atrial septal defects/holes, which are in some cases called Eisenmenger complex, as well as valve conditions such as stenosis.

Pulmonary hypertension can be associated with left heart disease, or right heart disease. In some embodiments, paliperidone can be used to treat pulmonary hypertension associated with left heart disease, whereas in other embodiments, paliperidone can be used to treat pulmonary hypertension associated with right heart disease. In further embodiments, paliperidone can be used to treat pulmonary hypertension associated with both right and left heart disease.

Pulmonary hypertension can be characterized by a pulmonary blood pressure greater than about 25 mm Hg at rest, and 30 mm Hg during exercise. Normal pulmonary arterial pressure is about 14 mm Hg at rest. In certain embodiments, paliperidone can be used to treat patients having a resting pulmonary arterial pressure of at least 20 mm Hg, at least 25 mm Hg, at least 30 mm Hg, at least 35 mm Hg, at least 40 mm Hg, at least 45 mm Hg, at least 50 mm Hg, at least 55 mm Hg, or at least 60 mm Hg.

The term "Paliperidone" is used in the broad sense to include its pharmaceutically acceptable esters and salts thereof. Paliperidone may be administered as the free base/free hydroxyl, or it may be administered as an ester or salt. Suitable esters are those at the 9-hydroxy position, including those formed from $C_{1-20}$ carboxylic acids. Suitable esters include methyl and ethyl. Other suitable esters include propyl, butyl, pentyl, hexyl, heptyl, octyl, nonyl, decyl, undecyl, dodecyl, $C_{13}$, $C_{14}$, $C_{15}$, $C_{16}$, $C_{17}$, $C_{18}$, $C_{19}$ and $C_{20}$ esters, including linear, branched and cyclic esters. In some cases the ester can be made from a fatty acid, for instance, stearyl, lauryl, olelyl, and palmityl. Palmityl esters can be especially preferred, for instance, paliperidone palmitate. Other esters include phosphate and phosphonate. The ester can be ionic, e.g., anionic or cationic, to improve water solubility or other pharmacokinetic property. Functionalized esters, for instance those obtained from amino acids can also be used. Suitable pharmaceutically acceptable derivatives and/or pharmaceutically acceptable salts include but are not limited to pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable tautomers, pharmaceutically acceptable complexes etc.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

Preferably, the composition of the instant invention may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution, transdermal patches and sprinkles, other dosage forms such as controlled release formulations, lyophilized formulations, modified release formulations, delayed release formulations, extended release formulations, pulsatile release formulations, dual release formulations and the like. Liquid or semisolid dosage form (liquids, suspensions, solutions, dispersions, ointments, creams, emulsions, microemulsions, sprays, patches, spot-on), injection preparations, parenteral, topical, inhalations, buccal, nasal etc. may also be envisaged under the ambit of the invention.

Suitable excipients may be used for formulating the dosage forms according to the present invention such as, but not limited to, stabilizers or surfactants, surface modifiers, wetting agents, suspending agents, isotonizing agents, chelating agents, osmolality adjusters, pH adjusters, emulsifiers, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, anti-microbial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof. Certain specific excipients may be used for specific dosage forms, as per the requirement of the invention.

In some instances, paliperidone can be administered by inhalation, for instance as a powder or aerosolizable formulation.

The bioavailability of the drug in a composition, depends on various attributes of the drug as well as the other inactive ingredients in the formulation. The particle size of the drug is one of such attribute that may affect the bioavailability of the drug, when administered to a patient. The particle size may thus be adjusted as per the requirements of the invention.

The dosage and dosage regimen may be calculated per kg body weight. The dosage regimen may vary from a day to a month. Accordingly, the initial dosage and maintenance doses may be specified. The dose as contemplated as per the instant invention can be in the range of 0.01 to 1000 mg. The preferable dose according to the instant invention can be in the range of 0.05 to 500 mg.

Preferably, the composition as contemplated by the invention may be administered at least once, twice or thrice a day, in a dosing range of 0.1 mg to 50 mg or as per the requirement of the patient to be treated.

On administration, Paliperidone palmitate hydrolyzes to the active moiety, Paliperidone. The dose calculation is done taking the above into consideration. Thus, 39 mg Paliperidone palmitate would provide 25 mg Paliperidone, 78 mg Paliperidone palmitate would provide 50 mg Paliperidone, etc.

Disclosed herein are methods for treating patients with pulmonary arterial hypertension. The hypertension may be mild (resting arterial pressure between 14-25 mm Hg) or complete (resting arterial pressure greater than 25 mm Hg). The patient to be treated may have a pulmonary arterial pressure greater than 14 mm Hg, greater than 16 mm Hg, greater than 18 mm Hg, greater than 20 mm Hg, greater than 22 mm Hg, greater than 24 mm Hg, greater than 26 mm Hg, greater than 28 mm Hg, greater than 30 mm Hg, greater than 32 mm Hg, greater than 34 mm Hg, greater than 36 mm Hg, greater than 38 mm Hg, or greater than 40 mm Hg.

Paliperidone can be used to treat patients with sporadic idiopathic PAH, heritable PAH, as well as PAH due to disease of small pulmonary muscular arterioles In some embodiments, paliperidone is administered to a patient (which may be a human or other mammal) in an amount sufficient to cause at least a 5%, 10%, 15%, 20%, 25%, 30%, 35%, or 40% reduction in resting arterial pressure relative to the pulmonary arterial pressure prior to commencing treatment. In some instances, paliperidone is administered at a dose effective such that the patient's final resting arterial pressure is about 25 mm Hg, about 24 mm Hg, about 23 mm Hg, about 22 mm Hg, about 21 mm Hg, about 20 mm Hg, about 19 mm Hg, about 18 mm Hg, about 17 mm Hg, about 16 mm Hg, about 15 mm Hg, or about 14 mm Hg. In certain embodiments, paliperidone is administered in combination with other agents, as described below, to achieve these therapeutic outcomes.

In some instances, the paliperidone may be administered to a patient a single time, while in other cases paliperidone can be administered using an intervallic dosing regimen. For instance, paliperidone may be administered once, twice, or three times a day for a period at least 1 week, for example 2 weeks, 4 weeks, 6 weeks, 8 weeks, 10 weeks, 20 weeks, 40 weeks, or 52 weeks. In some instances, paliperidone administration can be suspended for some period of time (e.g., 1, 2, 3, 4, 6, 8, 10, 20, 40 or 52 weeks) followed by another period of administration.

In some instances, the paliperidone can be administered to the patient using an interval greater than a day. For instance, the paliperidone can be administered once every other day, once every third day, once a week, once every two weeks, once every four weeks, once a month, once every other month, once every third month, once every six months, or once a year. In some instance injectable formulations, such as depot formulations, are suitable for dosing regimens with extended periods in between administration, however, oral formulations can also be used in such systems.

As pointed out earlier, there are various other drugs that are currently being used to treat PAH. One of such drugs is Sildenafil, which is marketed as Revatio by Pfizer. Revatio is available as film coated tablets, as an injection as well as oral suspension. Sildenafil is an inhibitor of cGMP specific phosphodiesterase type-5 (PDE-5) in the smooth muscle of the pulmonary vasculature, where PDE-5 is responsible for degradation of cGMP. Sildenafil, therefore, increases cGMP within pulmonary vascular smooth muscle cells resulting in relaxation. In patients with PAH, this can lead to vasodilation of the pulmonary vascular bed and, to a lesser degree, vasodilatation in the systemic circulation. Studies in vitro have shown that sildenafil is selective for PDE-5. In addition to pulmonary vascular smooth muscle and the corpus cavernosum, PDE-5 is also found in other tissues including vascular and visceral smooth muscle and in platelets. The inhibition of PDE-5 in these tissues by sildenafil may be the basis for the enhanced platelet anti-aggregatory activity of nitric oxide observed in vitro, and the mild peripheral arterial-venous dilatation in vivo.

In certain embodiments, paliperidone can be co-administered with one or more additional agents effective to lower pulmonary hypertension. In some embodiments the co-administration includes a unitary dosage form containing paliperidone and at least one more agent. In other embodiments, paliperidone is administered separately from the other agent(s). The additional agent can be a PDE-5 inhibitor, for example, avanafil, lodenafil, mirodenafil, sildenafil, tadalafil, vardenafil, udenafil, zaprinast, or icariin. Other agents include calcium channel blockers like dihydropyridines (e.g., amlodipine, nifefipine) and diltiazem; prostacyclin pathway agonists such as epoprostenol, treprostinil, iloprost, and selexipag; endothelin receptor antagonists such as bosentan, macitentan, ambrisentan, andsitaxsentan; guanylate cyclase stimulators such as riociguat; diuretics; toprimate; fusadil; or anti-coagulants like warfarin.

In order that this invention is more fully understood, the following preparative and testing methods and examples are set forth. These methods are for the purpose of illustration only and are not to be construed as limiting the scope of the invention in any way.

EXAMPLES

Example 1: Pulmonary Arterial Hypertension Efficacy Model

The studies were conducted for Hemodynamic Evaluation of Paliperidone palmitate in Anesthetized Sprague Dawley Rats Treated with Monocrotaline to Induce Pulmonary Arterial Hypertension. Sildenafil was used as an internal control to compare the effects of Paliperidone palmitate.

Method (Monocrotaline Rat)

Adult male Sprague-Dawley rats (287±4 g) were obtained from Charles River Laboratories (Raleigh, N.C.). Animals housed individually in a temperature/humidity controlled room with 12-hour light/dark cycles, had free access to water and food and were acclimated for one week prior to the study. Rats were randomly assigned (n=10 per group).

Rats in groups 1 and 2 served as healthy controls; the remaining rats were injected subcutaneously on Day 0 with 60 mg/kg body weight monocrotaline, the toxic alkaloid of *Crotalaria spectabilis*, (dissolved in DMSO at a concentration of 60 mg/ml, Sigma Aldrich, St. Louis, Mo.). On days 1-21, the rats were dosed via oral gavage (2 ml/kg) with vehicle (PBS), or the test compound—Paliperidone palmitate. Rats were weighed daily, and the dosages of test compound adjusted appropriately.

Monocrotaline (MCT) is an 11-membered macrocyclic pyrrolizidine plant alkaloid. A single SQ injection into rats results in hepatic generation of toxic metabolite—MCT pyrrole. Phase II metabolism of MCT is through glutathione conjugation. Reactive metabolite is transported to lungs, injuring pulmonary vasculature.

The effects of sildenafil and Paliperidone palmitate were evaluated in rats with monocrotaline induced pulmonary arterial hypertension. Male Sprague-Dawley rats were orally administered vehicle, Paliperidone palmitate (1.25 or 3.75 mg/kg, once every day for 28 days starting on Day 1, or sildenafil (30 mg/kg, administered twice daily) (n=10 in each group). Rats received a single injection of monocrotaline (60 mg/kg, s.c.) on Study Day 1. On the twenty-eighth day following monocrotaline dosing, the rats were anesthetized with ketamine/xylazine for terminal monitoring of pulmonary and systemic arterial pressures along with heart rate.

The Table 1 gives the study design for the test article and vehicle administrations.

The results with Paliperidone palmitate were comparable to those with Sildenafil.

The table 2 gives normal cardiovascular parameters in SD rats.

TABLE 2

| Parameter<br>Mean ± SEM | Treatment Cohort - Vehicle<br>(mg/kg)<br>DMSO |
|---|---|
| Systolic PAP (mm Hg) | 16 ± 2 |
| Mean PAP (mm Hg) | 14 ± 2 |
| MAP (mm Hg) | 84 ± 9 |
| HR (bpm) | 313 ± 13 |
| Heart Wt (g) | 1.17 ± 0.03 |
| HW/BW | 2.75 ± 0.07 |
| LV Wt (g) | 0.82 ± 0.01 |
| RV Wt (g) | 0.22 ± 0.02 |
| Lung Wt (g) | 1.65 ± 0.08 |
| RV/LV + S | 0.26 ± 0.02 |
| RV/BW | 0.50 ± 0.03 |
| Body Weight (kg) | 0.43 ± 0.01 |

The table 3 provides the effect of Paliperidone palmitate/Sildenafil in rats with monocrotaline induced PAH.

TABLE 1

| Group | Test Compound | Test Compound Dose Level (mg/kg) | Dose Conc. (mg/mL) | Dose Volume (mL/kg) | Dose Period | Dose Route | Dose Days | No. of Male Rats |
|---|---|---|---|---|---|---|---|---|
| 2-5 | Monocrotaline[1] | 80 | 80 | 1 | AM | SC | 1 | 100 |
| 1 | DMSO[2] | NA | NA | 1 | AM | SC | 1 | 5 |
| 2 | Vehicle | NA | NA | 5 | AM | Oral | 1-28 | 10 |
| 3 | Paliperidone palmitate | 1.25 | 0.25 | 5 | AM | Oral | 1-28 | 10 |
| 4 | Paliperidone palmitate | 3.75 | 0.75 | 5 | AM | Oral | 1-28 | 10 |
| 5 | Sildenafil | 30<br>30 | 6<br>6 | 5<br>5 | AM<br>PM | Oral | 1-28 | 10 |

[1]Single dose in DMSO administered 28 days prior to terminal procedure.
[2]Single dose administered 28 days prior to terminal procedure.

Results

There were differences in systolic and mean pulmonary arterial pressures after 28 days in rats treated with Paliperidone palmitate compared to the vehicle group. Rats treated with Paliperidone palmitate showed a 25% and 20% reduction at 1.25 and 3.25 mg/kg dosing, respectively, in systolic pulmonary arterial pressure—the variable used as an arbiter of protection. The sildenafil group also showed protection, reducing SPAP by 23%. There was also a modest beneficial effect with respect to right ventricular hypertrophy (as measured by RV/LV+S—Fulton's Index) in both Paliperidone palmitate groups (−12% and −7% at 1.25 and 3.75 mg/kg, respectively) and to a similar degree the sildenafil (−14%) cohort compared to vehicle. When correcting RV (wt) by body weight, Paliperidone palmitate showed a 19% decrease in hypertrophy at either dose. Sildenafil had a 21% decrease in this hypertrophic index, respectively. No substantive differences in heart rate or mean arterial pressure were noted for rats treated with Paliperidone palmitate or sildenafil compared to vehicle.

TABLE 3

| Parameter<br>Mean ± SEM | Treatment Cohort - Monocrotaline (mg/kg) | | | |
|---|---|---|---|---|
| | Vehicle | Paliperidone palmitate 1.25 | Paliperidone palmitate 3.75 | Sildenafil 60/day bid |
| Systolic PAP (mm Hg) | 60 ± 2 | 45 ± 3 | 48 ± 3 | 46 ± 7 |
| Mean PAP (mm Hg) | 46 ± 1 | 34 ± 1 | 39 ± 3 | 38 ± 6 |
| MAP (mm Hg) | 70 ± 6 | 54 ± 9 | 68 ± 5 | 69 ± 5 |
| HR (bpm) | 274 ± 10 | 253 ± 36 | 312 ± 12 | 278 ± 21 |
| Heart Wt (g) | 1.36 ± 0.05 | 1.28 ± 0.03 | 1.28 ± 0.06 | 1.24 ± 0.02 |
| HW/BW | 4.43 ± 0.15 | 3.94 ± 0.22 | 3.92 ± 0.21 | 3.89 ± 0.17 |
| LV Wt (g) | 0.78 ± 0.01 | 0.77 ± 0.01 | 0.73 ± 0.03 | 0.74 ± 0.02 |
| RV Wt (g) | 0.46 ± 0.02 | 0.39 ± 0.02 | 0.40 ± 0.03 | 0.38 ± 0.02 |
| Lung Wt (g) | 2.90 ± 0.53 | 2.59 ± 0.13 | 2.23 ± 0.04 | 2.36 ± 0.13 |
| RV/LV + S | 0.59 ± 0.03 | 0.52 ± 0.04 | 0.55 ± 0.06 | 0.51 ± 0.03 |

TABLE 3-continued

| | Treatment Cohort - Monocrotaline (mg/kg) | | | |
|---|---|---|---|---|
| Parameter Mean ± SEM | Vehicle | Paliperidone palmitate 1.25 | Paliperidone palmitate 3.75 | Sildenafil 60/day bid |
| RV/BW | 1.50 ± 0.06 | 1.22 ± 0.10 | 1.22 ± 0.12 | 1.19 ± 0.09 |
| Body Weight (kg) | 0.31 ± 0.02 | 0.33 ± 0.02 | 0.33 ± 0.02 | 0.32 ± 0.01 |

Paliperidone palmitate was shown to prevent the development of PAH in the rat monocrotaline (MCT) model. Thus, Paliperidone palmitate, a novel antagonist of dopamine D2 receptor and the serotonin 5-HT2A receptor, when administered to rats for three weeks in daily oral doses, prevents not only monocrotaline (MCT)-induced elevations in pressure in the pulmonary arterial circuit but also hypertrophy of the right ventricle.

Example 2: Process for Formulating the Paliperidone Palmitate Composition According to the Invention 1) Sift Microcrystalline cellulose, Lactose monohydrate and Croscarmellose sodium through an appropriate sieve,
2) Sift Paliperidone palmitate through an appropriate sieve,
3) Load the materials of step 1 & 2 in a suitable mixer granulator and mix,
4) Prepare Polysorbate-80 solution by dissolving it in part quantity of methylene chloride/water,
5) Prepare the binder solution by dissolving Povidone in remaining quantity of methylene chloride/water,
6) Granulate the dry mix of step 3 with the binder solution of step 5 in a rapid mixer granulator till the wet mass of suitable consistency is obtained,
7) Dry the granules in a fluidized bed drier until the desired LOD is achieved,
8) Size the dried granules using an appropriate sieve,
9) Blend the granules of step 8 with sifted Hypromellose, sifted Silicon dioxide and sifted Talc,
10) Blend required quantity of sifted Magnesium stearate with the blend of step 9,
11) Compress the blend of step 10 into tablets using suitable punches,
12) Film coat the compressed tablets with Opadry ready mix.

Example 3: Pharmaceutical Composition Prepared Using the Process in Example 2

| Sr. No. | Ingredients | Qty/Tab (mg) |
|---|---|---|
| 1 | Paliperidone palmitate | 0.5-50 |
| 2 | Microcrystalline cellulose | 10-35 |
| 3 | Lactose Monohydrate | 50-200 |
| 4 | Croscarmellose Sodium | 2-10 |
| 5 | Povidone | 3-10 |
| 6 | Polysorbate 80 | 3-10 |
| 7 | Methylene chloride/water | q.s. |
| 8 | Hypromellose | 30-90 |
| 9 | Colloidal silicon dioxide | 1-5 |
| 10 | Talc | 1-5 |
| 11 | Magnesium Stearate Coating | 1-5 |
| 12 | Opadry ready mix | 10-20 |
| 13 | Purified water | qs |

Example 4: Process for Formulating the Paliperidone Palmitate Composition According to the Invention 1. Sift microcrystalline cellulose, dibasic calcium phosphate and Croscarmellose sodium through an appropriate sieve,
2. Sift Paliperidone palmitate through an appropriate sieve,
3. Load the materials of step 1 & 2 in a suitable mixer granulator and mix,
4. Dissolve Polyvinyl pyrrolidone in required quantity of purified water.
5. Granulated the blend of step 3 using binder solution of step 4,
6. Dry the granules in fluidized bed drier until the desired LOD is reached,
7. Size the dried granules by passing through an appropriate sieve,
8. Blend the sized granules with sifted Colloidal silicon dioxide,
9. Blend the required quantity of sifted Magnesium stearate with the blend of step 8,
10. Compressed the blend of step 9 into tablets using suitable punches using tablet compression machine.

Example 5: Pharmaceutical Composition Prepared Using the Process in Example 4

| Sr. No. | Ingredients | Quantity Mg/tablet |
|---|---|---|
| 1) | Paliperidone palmitate | 0.5-50 |
| 2) | Microcrystalline cellulose (Avicel PH 102) | 40-100 |
| 3) | Dibasic calcium phosphate anhydrous | 30-120 |
| 4) | Croscarmellose sodium (Ac-Di-sol) | 5-20 |
| 5) | Poly vinyl pyrrolidone (PVP-K30) | 10-25 |
| 6) | Purified water | QS |
| 7) | Colloidal silicon dioxide (Aerosil 200) | 1-5 |
| 8) | Magnesium stearate | 2-8 |

It will be readily recognized by a person skilled in the art that varying substitutions and modifications may be made to the invention disclosed herein without departing from the spirit of the invention. Thus, it should be understood that although the present invention has been specifically disclosed by the preferred modification and variation of the concepts herein disclosed may be resorted to by those skilled in the art, and such modifications and variations are considered to be falling within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The invention claimed is:

1. A pharmaceutical composition comprising:
   paliperidone or a pharmaceutically acceptable salt or ester thereof; and
   at least one additional agent effective to treat pulmonary arterial hypertension, wherein the additional agent is selected from the group consisting of a PDE-5 inhibitor, a calcium channel blocker, a prostacyclin pathway agonist, an endothelin receptor antagonist, a guanylate cyclase stimulator, a diuretic, an anti-coagulant, and combinations thereof.

2. The pharmaceutical composition according to claim 1, comprising a PDE-5 inhibitor selected from the group consisting of avanafil, lodenafil, mirodenafil, sildenafil, tadalafil, vardenafil, udenafil, zaprinast, icariin, and combinations thereof.

3. The pharmaceutical composition according to claim 1, comprising a calcium channel blocker selected from the group consisting of amlodipine, nifefipine, diltiazem and combinations thereof.

4. The pharmaceutical composition according to claim 1, comprising a prostacyclin pathway agonist selected from the group consisting of epoprostenol, treprostinil, iloprost, selexipag, and combinations thereof.

5. The pharmaceutical composition according to claim 1, comprising an endothelin receptor antagonist selected from the group consisting of bosentan, macitentan, ambrisentan, sitaxsentan, and combinations thereof.

6. The pharmaceutical composition according to claim 1, comprising riociguat.

7. The pharmaceutical composition according to claim 1, comprising a diuretic selected from the group consisting of toprimate, fasudil fusadil, and combinations thereof.

8. The pharmaceutical composition according to claim 1, comprising warfarin.

9. The pharmaceutical composition according to claim 1, comprising paliperidone palmitate.

10. The pharmaceutical composition according to claim 1, wherein the composition is a tablet or capsule.

11. The pharmaceutical composition according to claim 1, wherein the composition is a suspension or solution.

12. The pharmaceutical composition according to claim 1, wherein the composition is an aerolizable powder.

* * * * *